United States Patent [19]
Simonson

[11] Patent Number: 6,159,179
[45] Date of Patent: Dec. 12, 2000

[54] CANNULA AND SIZING AND INSERTION METHOD

[76] Inventor: Robert E. Simonson, 799 NE. 71ST St., Boca Raton, Fla. 33487

[21] Appl. No.: 09/266,984

[22] Filed: Mar. 12, 1999

[51] Int. Cl.⁷ ................................................. A61M 5/00
[52] U.S. Cl. .......................... 604/117; 604/164; 604/500
[58] Field of Search .................................. 604/117, 164, 604/264, 523, 500, 533, 534

[56] References Cited

U.S. PATENT DOCUMENTS

| | | |
|---|---|---|
| 4,862,891 | 9/1989 | Smith . |
| 4,863,423 | 9/1989 | Wallace ..................................... 604/48 |
| 5,106,376 | 4/1992 | Mononen et al. ...................... 604/164 |
| 5,158,543 | 10/1992 | Lazarus . |
| 5,279,567 | 1/1994 | Ciaglia et al. ........................... 604/117 |
| 5,292,309 | 3/1994 | Van Tassel et al. .................... 604/117 |
| 5,431,639 | 7/1995 | Shaw ....................................... 604/264 |
| 5,472,426 | 12/1995 | Bonati et al. . |
| 5,489,274 | 2/1996 | Chu et al. ................................ 604/167 |
| 5,611,778 | 3/1997 | Brinon .................................... 604/117 |
| 5,792,044 | 8/1998 | Foley et al. . |
| 5,954,635 | 9/1999 | Foley et al. . |

Primary Examiner—John D. Yasko
Attorney, Agent, or Firm—Norman Friedland

[57] ABSTRACT

A relatively inexpensive cannula is sized by including indica on a cannulated dilator that is used to measure the depth of a body cavity, and in one embodiment with the use of a cuttable fixture inserted into an initially enlarged dilator retractor made from a cuttable material the excess of the dilator retractor is snipped by a commercial cutter. A tool engaging the end of the cannulated dilator provides leverage on the cannulated dilator for rotation as it is forced into the body cavity, a pusher tool provides leverage on the dilator retractor for inserting the dilator retractor into the body cavity. A clamp that fits the top of the dilator retractor serves to support the dilator retractor through an arm to a rigid structure. In an alternate embodiment one of a series of sized dilator retractors are selected commensurate with the measurement attained by the scaled cannulated dilator.

24 Claims, 4 Drawing Sheets

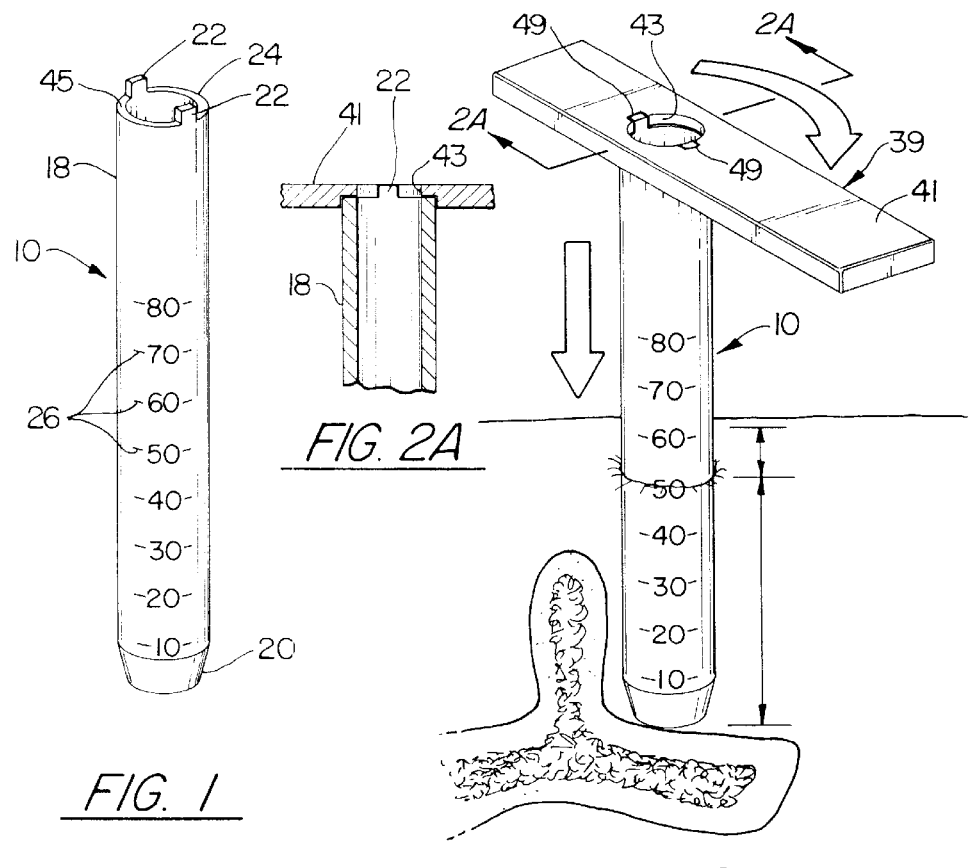
FIG. 1
FIG. 2A
FIG. 2
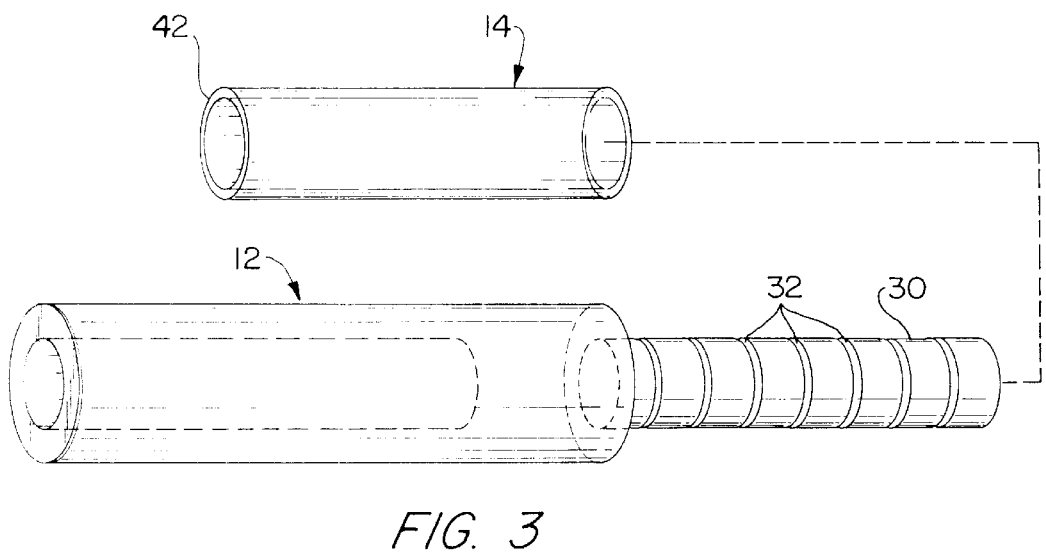
FIG. 3

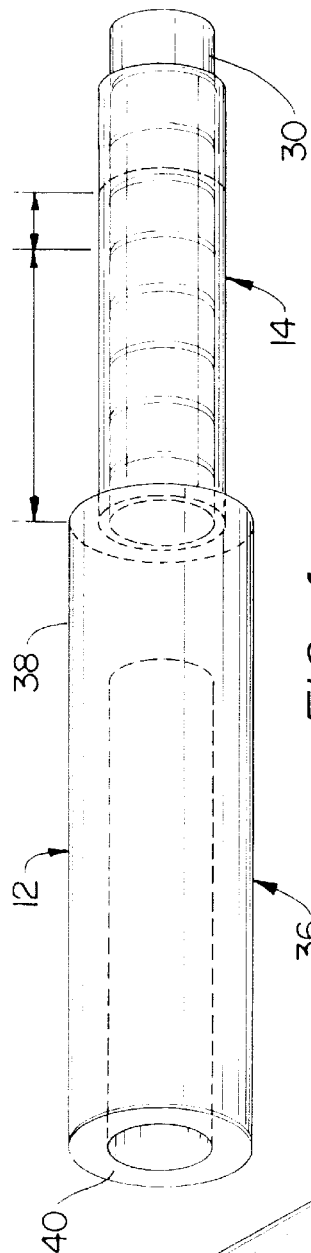
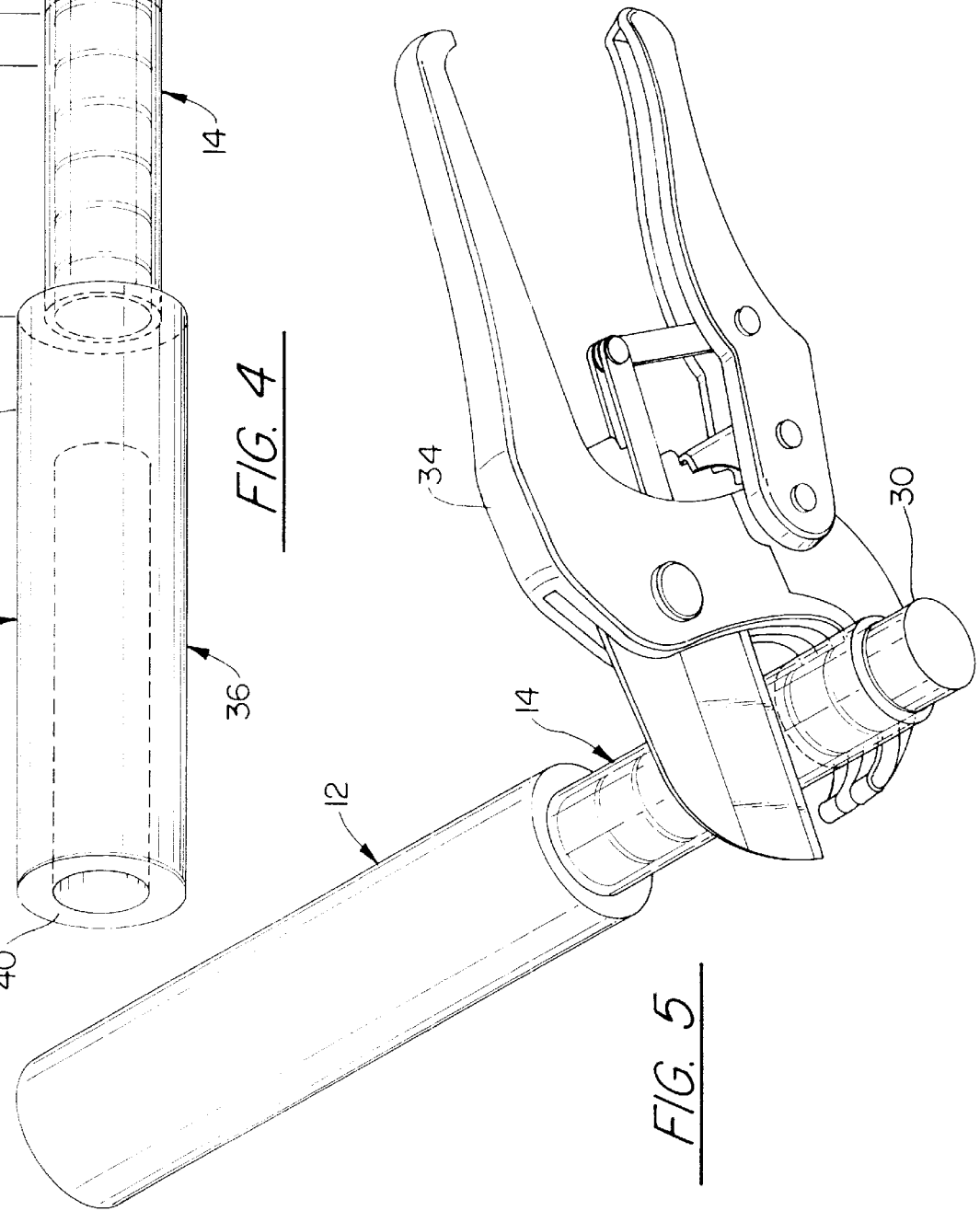

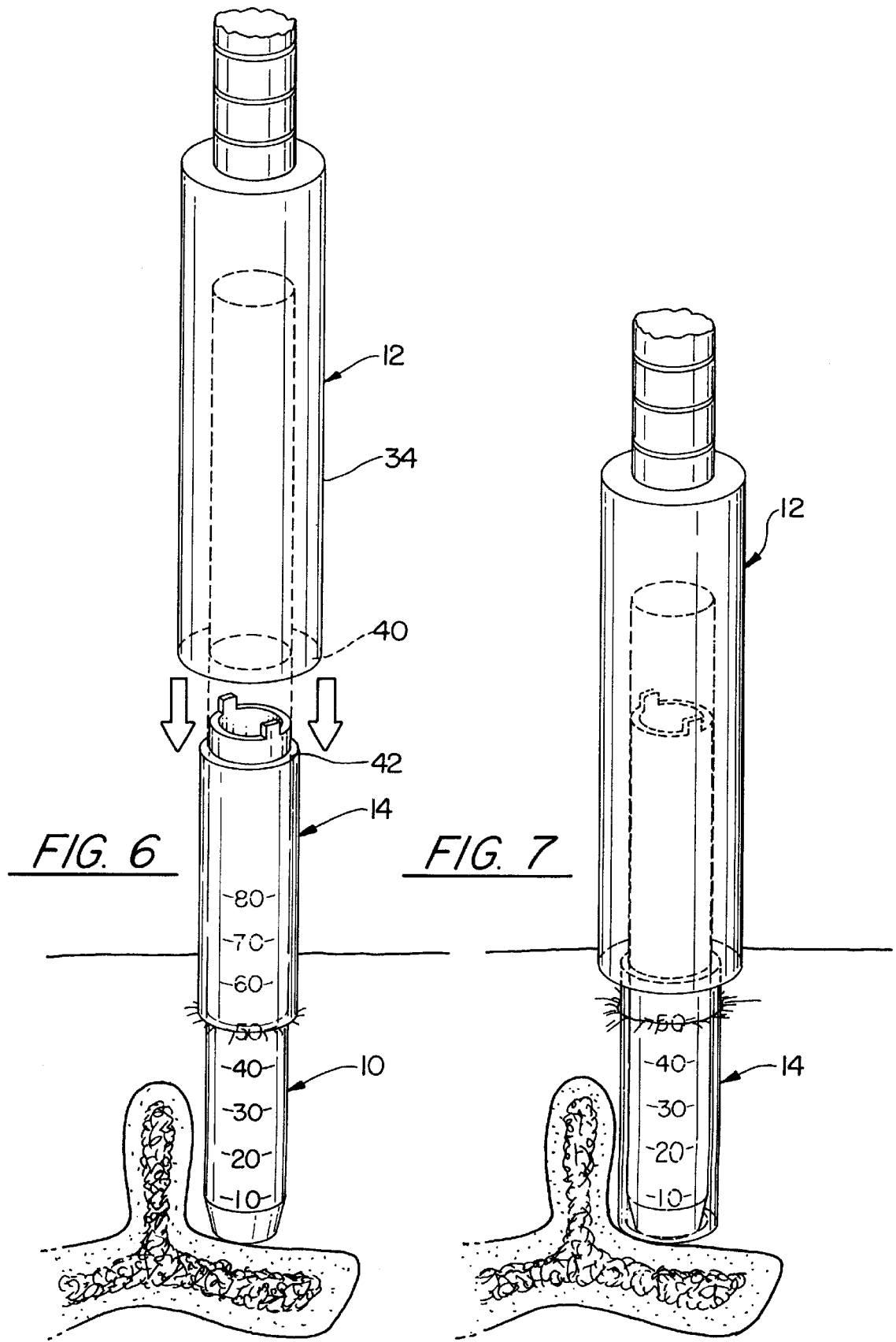

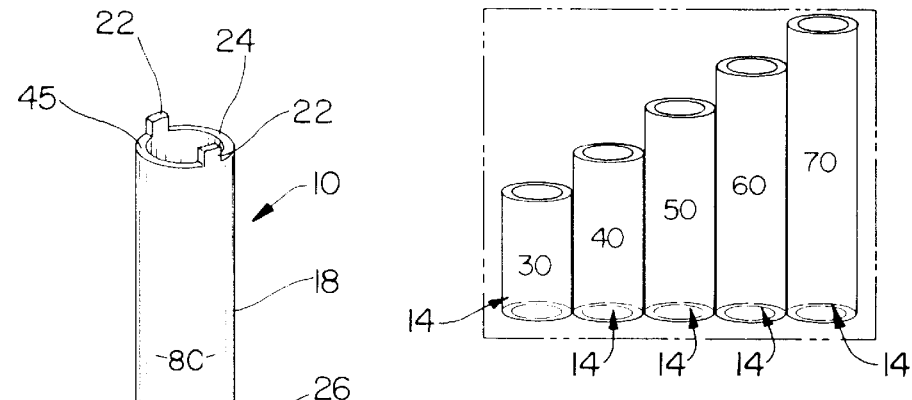
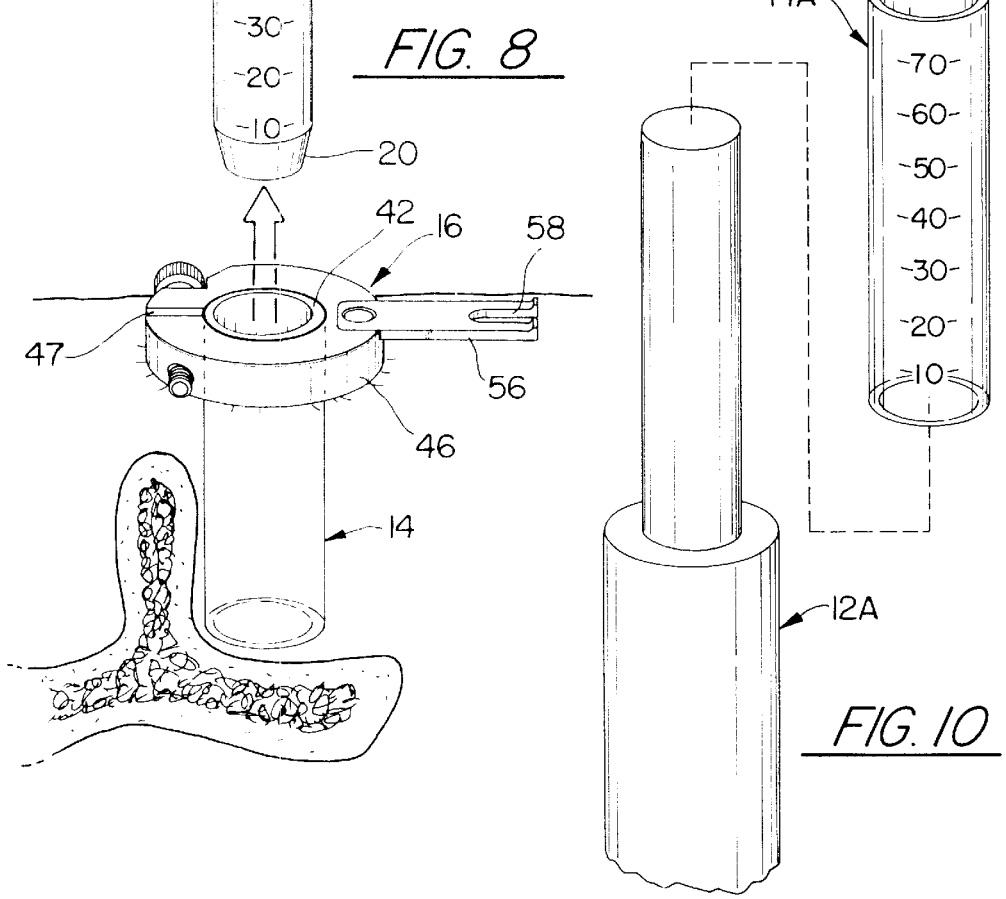
FIG. 8
FIG. 9
FIG. 10

CANNULA AND SIZING AND INSERTION METHOD

TECHNICAL FIELD

This invention relates to a cannula and cannulated dilator and more particularly to a cannula intended to be utilized in surgery on a patient which cannula is sized by the measurement obtained from the cannulated dilator for obtaining a desired length of the cannula inserted into the body cavity of the patient for ease of the surgical procedure being preformed by the surgeon and the apparatus for insertion of the cannulated dilator and the dilator retractor into the body cavity.

BACKGROUND OF THE INVENTION

As is known in the medical field, the cannula is utilized for creating a passage extending from the exterior into a cavity in the patient to a particular location where the surgical procedure is to be performed. For example, in current day practices lumbar discectomy whose objective is to decompress the affected nerve root, endoscopic and micro endoscopic techniques are often used. These techniques are becoming popular inasmuch as the patient benefits from the small incision, limited tissue disruption, better visualization and illumination all of which shortens the hospital stay and hastens recovery. One of the techniques for performing the lumbar discectomy is the use of tubular retractor (a specific cannula) which allows for laminotomy, deical facetectomy, foraminotomy, nerve root retraction and disectomy. A typical procedure is to advance a guidewire through a small incision which is advanced to the inferior edge of the superior lamina. A small incision is then made that extends either cranially or caudally. A calnulated dilator is then inserted over the guidewire. Larger diameter cannulated dilators are sequentially inserted over each other to increase the opening into the body cavity. Typically the guide wire is removed after the first cannulated dilators installed and eventually the cannulated dilators are all removed after the, tubular retractor has been inserted over the largest of the cannulated dilators. Once these procedures are accomplished, the tubular retractor is locked into position by a retractor clamp that is clamped to a retractor clamping arm which is fixed to a rigid member such as the operating table. This provides an unencumbered zone where the surgeon can perform the medical procedure that was intended to be performed.

As is well known in this field of technology, the cannulated dilators and tubular retractors are made from surgical metal material and are sized for the largest depth that is anticipated in the surgical procedure. Hence, whether the depth is 10 millimeters (mm), 20 mm, 30 mm, etc. Measured from the exterior of the cavity to the most interior position in the cavity (inferior edge of the superior lamina) the tubular retractor that may be available for use ii the surgical procedure could be 100 mm or larger. The additional or excess length of the dilator retractor is not only cumbersome to use, it is unnecessary and undesirable.

This invention obviates this problem by providing the necessary elements that allow the dilator retractor (cannula) to be cut to size once the incision and diameter of the cavity has been established. Hence, in the surgical procedure described above the last cannulated dilator in the procedure in accordance with this invention includes indicia of a graduated vertical scale on the tubular wall, preferably in millimeters that is viewed by the user. A cannula or dilator retractor, which basically is a cylindrical tube made from a plastic or synthetic material in one preferred embodiment or surgical metal in another embodiment which is easy to cut and which is transparent in one embodiment and opaque in another is provided in the largest length contemplated in this particular procedure or alternatively is pre-sized in a series of sized cannulas. A template that has a diameter that is slightly smaller than the diameter of the dilator retractor made from a soft plastic material such as Teflon material that may include graduated annular grooves that are graduated vertically in scale that is commensurate with the indicia scale on the cannulated dilator. Or alternatively, the dilator retractor may also include on the wall indicia corresponding to the indicia on the cannulated dilator. Hence, the surgeon or user merely has to count the annular grooves or the indicia on the wall of the dilator retractor to match the depth of the cavity and with a cutter, cut through the delator retractor which will provide a cannula that is acceptable to the surgeon without the unnecessary length that has heretofore presented a problem.

An annular retractor clamp is provided to fit over the top of the dilator retractor which obviously is sized to accommodate the width of the retractor clamp which, in turn, is utilized to mate with a rigid holder that is clamped to a rigid member such as the operating table or other convenient member to secure the cannula in place.

This invention also contemplates a tool for insertion of the cannulated dilator and a tool for the insertion of the dilator retractor into the body cavity. The tool for insertion of the cannulated dilator is a rectangular shaped planar member that removably fits the cannulated dilator and serves to provide leverage for the surgeon to turn the dilator retractor while it is being inserted into the body cavity to reach its ultimate destination. A tool for insertion of the dilator retractor is generally a pusher which may be made integral with the template includes an inner bore that is slightly larger than the outer diameter of the cannulated dilator and includes a flat bottom surface that overlies the top end wall surface of the dilator retractor so that the pusher provides leverage for the surgeon to slide the dilator retractor over the scaled cannulated dilator until it reaches the final destination in the body cavity.

As an alternate to the use of the cutter and template, it is contemplated within the scope of this invention, that a series of different length dilator retractors will be made available so that the surgeon after making the measurement of the depth of body cavity with the cannulated dilator will select the dilator retractor that most closely matches the size desired.

SUMMARY OF THE INVENTION

An object of this invention is to provide a dilator retractor that is sized to fit the patient for use in a surgical procedure.

A feature of this invention is to provide indicia of a vertical scale on the cannulated dilator to ascertain the depth of the cavity in the body in which a medical procedure is to be performed. In one embodiment a template made from a relatively soft plastic material fits into the dilator retractor having a scale commensurate with the scale on the cannulated dilator for supporting the dilator retractor as it is cut to the desired length. In another embodiment the dilator retractor includes indicia on the outer surface that correlates to the indicia on the cannulated dilator. In one embodiment the dilator retractor is transparent, in another embodiment it is opaque, and it can be made from either plastic or metallic material when in the opaque embodiments.

Another feature of this invention is the provision of a tool that is adapted to fit the cannulated dilator to allow the surgeon to turn the cannulated dilator as the surgeon pushes the cannulated dilator into the body cavity against the resistance of the body tissue. In one embodiment the tool includes concentric bores that define a shoulder that engages the end of the cannulated dilator and recesses that engage tabs axially extending from the proximate end of the cannulated dilator.

An alternative to the cutting procedure is the provision of predetermined different length dilator retractors that permit the surgeon to select the desire length commensurate with the depth of the body cavity.

Another feature of this invention is an annular retractor clamp that is slidable over the outer surface of the dilator retractor that is locked into place and adaptable to fit onto a flexible arm that is rigidly connected to a static structure such as the operating table.

The foregoing and other features of the present invention will become more apparent from the following description and accompanying drawings.

BRIEF DESCRIPTION OF THE DRAWINGS

FIG. 1 is a perspective view in elevation showing the details of the cannulated dilator of this invention;

FIG. 2 is a perspective view in elevation and section of the cannulated dilator inserted into the cavity of a body and extending to the inferior edge of the superior lamina and a turning tool adapted to retractor clamp onto the tabs extending from the proximate end of the cannulated dilator;

FIG. 2A is a partial view in cross section taken along the lines 2A—2A of FIG. 2;

FIG. 3 is an exploded view in perspective illustrating the dilator retractor being fitted onto the graduated template and pusher prior to being cut to the desired length;

FIG. 4 is a view in perspective illustrating the dilator retractor fitted onto the template;

FIG. 5 is a view in perspective illustrating the dilator retractor being cut by a commercially available cutting tool;

FIG. 6 is a view in perspective illustrating the pusher for pushing the dilator retractor into the body cavity;

FIG. 7 is a view in perspective illustrating the pusher and dilator retractor of FIG. 6 when pushed to the destination;

FIG. 8 is a view in perspective of the dilator retractor and the retractor clamp and the cannulated dilator of this invention;

FIG. 9 is a view in perspective of a series of pre-sized dilator retractors made from an inexpensive material that as an alternative embodiment to the cut in situ dilator retractor; and FIG. 10 is a perspective exploded view similar to FIG. 3 showing another embodiment with the grooves in the template removed and the dilator retractor having indicia on the outer surface.

DETAILED DESCRIPTION OF THE INVENTION

While in the preferred embodiment this invention is being described in connection with a particular surgical procedure, namely, a lumbar disectomy, it is to be understood that this invention has utility in other types of procedures and as one skilled in this art can appreciate, the invention has particular utility where it is desirable to provide a length of the cannula that is commensurate with the depth of the body cavity. As used in this patent application the term "cannulated dilator" means a surgical instrument that is utilized to widen the body cavity and the term "dilator retractor" is a cannula intended to fit into the body cavity. As used throughout this disclosure the term "body cavity" unless indicated otherwise refers to an access hole formed in the body of the patient in order to reach the target where the medical procedure is being performed and the term cannula or dilator retractor serves to define a working cavity or chamber that the surgeon uses to perform a medical procedure. While in the preferred embodiment, it is preferred that the dilator retractor is made from a plastic material and is transparent as will be appreciated and as will be described herein below this invention contemplates a dilator retractor made from metallic material and in certain embodiments the material is opaque.

To best understand this invention reference is being made to FIGS. 1 through 8 which shows the cannulated dilator generally illustrated by reference numeral 10 (FIGS. 1, 2, 6, 8), the template and pusher tool instrument combination generally illustrated by reference numeral 12 (FIGS. 3–6), the dilator retractor generally illustrated by reference numeral 14 (FIGS. 3, 6, 7, 8) and the retractor clamp generally illustrated by reference numeral 16 (FIG. 8). As best seen in FIG. 1 the cannulated dilator 10 comprises a hollow tubular body 18 typically made from surgical metal such as surgical stainless steel, having a beveled end 20 at the distal end of the tubular body 18 and a pair of circumferentially spaced tabs 22 extending from the proximate end surface 24 of the tubular body 18. The beveled at the distal end 20 serves to help the insertion of the cannulated retractor 10 entering the body of the patient and the tabs 22 serve to fit into a tool that the surgeon utilizes to insert the cannulated dilator 10 as it progresses into the body until it reaches the inferior edge of the superior lamina as will be described in more detail hereinbelow. It is contemplated within the scope of this invention that other techniques for attaching the tool to the cannulated dilator 10 could be utilized, as for example a poly-sided recesses or reversal of the tabs by affixing them to the tool rather than the cannulated dilator and affixing complementary recesses in the cannulated dilator and other such techniques could be employed. What is contemplated by the tool is that it provides leverage to the user so that it allows the cannulated dilator to be turned while it is being pushed into the body cavity against the resistance of the body's tissues.

In accordance with this invention, indica 26 is placed on the exterior of the body 18 and is a graduated scale in millimeters (although any other unit of measurement can be utilized) that serves to indicate the depth of the body cavity and is used to determine the length of the dilator retractor 14 as will be described in more detail herein below. The dilator retractor 14 in one embodiment is made from a plastic material that is transparent and is sufficiently strong that exhibits hoop integrity that is capable of withstanding the forces of the tissue tending to exert a lateral force. This provides a relatively inexpensive member that is capable of being cut while the patient is in the operating room. In one embodiment the dilator retractor is fitted onto the fixture— and the fixture includes spaced grooves that are correlated to the measurement of the depth of the body cavity that is determined by the indicia of the cannulated dilator 10.

As mentioned above, once the depth of the body cavity as measured by the indicia on the cannulated dilator 10, the dilator retractor 14 is fitted on the scaled end of the template portion 30 which includes a series of annular grooves that are axially spaced a predetermined distance, say at 10 mm, so that the dilator retractor 14 being transparent in this instance, once fitted onto the template can be sized. Hence, the user merely counts the number of grooves that is commensurate with the measurement taken from the indicia of the cannulated dilator and the desired length is then cut to the desired length. Obviously, it is important that the dilator retractor 14 is initially oversized so that the length will be longer than any of the depths of the body cavity contemplated. Hence, in this manner the cannula is made to fit each individual patient. The technique for making the measurement and cutting to size is described as follows. If the depth of the body cavity measurement taken from the cannulated dilator was 30 mm the user would count 3 annular grooves which are spaced 10 mm apart to determine the length of the dilator retractor desired and would add an addition amount to compensate for the attachment dimension of the annular retractor clamp 18. Hence, if the width of the clamp 18 is 10 mm and the depth of cavity is 30 mm, the user would select 40 mm as the juncture where the dilator retractor is cut to size.

Once the length of the depth of the body cavity as calculated by the cannulated dilator 10 is determined and while the dilator retractor 14 is mounted on the fixture portion 30, and after the user determines the number of annular grooves on the fixture portion that will match the depth of the body cavity as measured by the indicia on the cannulated dilator and the amount necessary to hold the retractor clamp 18, the user with the use of the commercially available cutters 34 snips off the end of the retractor dilator 14. The fixture will also be cut and this system for cutting assures that the dilator retractor 14 will have a clean, smooth cut. A suitable cutter 34 is one that is available in many hardware stores such as Home Depot and is under the name "Orbit". This cutter was tested and has proven to work satisfactory. However, any type of cutter is contemplated for use with this invention, such as commercially available knives and pipe cutters, being other examples.

Once the dilator retractor 14 has been cut to size the dilator retractor 14 is then fitted over the cannula dilator 10 and is forced into the body cavity with a suitable pusher tool of the type shown in FIG. 4. Pusher tool portion 36 which in this instance is integral with the member 12 is formed on one end and includes the enlarged diameter portion 38 having a central axial bore that complements the outer diameter of the cannulated dilator 10. The bottom annular face 40 is formed with a flat surface that bears against the end 42 of the dilator retractor 14. This serves to provide leverage for the surgeon to push the dilator retractor 14 into the body cavity.

Also in accordance with this invention the end clamp 16 comprises an annular body 46 being split at 47 and including a threaded lateral bore that accommodates the tightening screw 50. The central opening is dimensioned to fit over the end of the dilator retractor 14 and slide thereon. Once in position the screw is tightened to secure the clamp to the dilator retractor 14. A bracket 56 having a bifurcated slot 58 serves to engage a flexible arm that is clamped to a rigid member. This serves to support the dilator retractor 14 while the surgeon is performing the surgical procedure.

FIG. 9 exemplifies another embodiment of this invention where the dilator retractors 14 come in a series of different sizes so that the surgeon after determining the size of the depth of the body cavity as ascertained by the graduated scale on the cannulated dilator 10, the surgeon merely selects the size to match the body cavity depth taking into consideration the extra length needed to accommodate the clamp 16.

The cannulated retractor tool 39 is a relatively rectangular flat member 41 having a central bore 43 that is made from two spaced diameters. The most inner diameter on the bottom face of the tool 39 is slightly larger than the outer diameter of the cannula dilator 10 and the outer diameter on the top face of the tool 39 is equivalent to the inner diameter of the cannulated dilator 10 to provide a shoulder for bearing on the annular top surface 45 of the cannulated dilator 10. A pair of concentrically spaced recesses 49 are formed in the top surface extending through the upper portion of tool 40 to accommodate and complement the tabs 22. Thus tool 39 serves to provide a leverage tool that helps the surgeon for forcing the cannulated dilator 10 into the body cavity and against the resistance created by the body tissue adjacent thereto.

FIG. 10 exemplifies another embodiment of this invention where the fixture 12a which is identical to fixture 12 does not include the spaced annular grooves and the cannula 14a which is identical to the cannula 14 includes indicia on the outer wall that corresponds to the indicia on the cannulated dilator 10. As is apparent from the foregoing the user merely has to size the cannula 14a by making a measurement of the body cavity with the cannulated dilator 10 and select the measurement corresponding thereto from the indicia on the cannula 14a, and after the cannula is inserted onto the fixture 12a, the user cuts the cannula 14a and fixture 12a so that the cannula 14a is sized to fit the body cavity. Obviously, the cannula 14a in this instance need not be transparent and can be opaque.

What has been described by this invention is a cannula that is sized to fit the individual patient. A cannulated dilator includes indicia of a scale for measuring the depth of the individual patient. With that measurement, the cannula in one embodiment may be made from a plastic, transparent material fits onto a fixture that is cuttable and contains a visible predetermined scale to cut the cannula to the particular length. In another embodiment the cannula includes indicia of a scale corresponding to the scale on the cannulated dilator and is similarly cut. The invention teaches a tool is provided to insert the cannulated dilator into the cavity and another tool to insert the cannula into the body cavity. In another embodiment a series of pre-sized cannulas are provided so that the user can select from this series the size that corresponds to the measurement obtained with the cannulated dilator.

Although this invention has been shown and described with respect to detailed embodiments thereof, it will be appreciated and understood by those skilled in the art that various changes in form and detail thereof may be made without departing from the spirit and scope of the claimed invention.

I claim:

1. A cannulated dilator having an outer surface, said cannulated dilator for insertion into an access hole formed in a patient for stretching the tissue adjacent to the access hole so as to enlarge the same, said cannulated dilator having an elongated tubular body, a beveled portion at the distal end thereof, the improvement comprising indicia on the side outer surface of the cannulated dilator for measuring the depth of the access hole, said cannulated dilator having a proximal end and a tool engagement portion formed thereon, in combination with a tool having an engagement portion complementing the tool engagement portion of the cannulated dilator adapted to fit thereon for rotation and applying leverage on said cannulated dilator for insertion thereof into the access hole and a cannula for fitting into said access hole for permitting the performance of a medical procedure after the cannulated dilator has been removed.

2. A cannulated dilator having an outer surface, said cannulated dilator for insertion into an access hole formed in the body of a patient for stretching the tissue adjacent the access hole and for enlarging the same, said cannulated dilator having an elongated tubular body, a beveled portion at the distal end thereof, the improvement comprising indicia on the side outer surface of the cannulated dilator for measuring the depth of the access hole, said cannulated dilator having a pair of circumferentially spaced tabs extending radially from the proximal end, in combination with a tool having a rectangularly shaped planar body, a central bore formed intermediate the ends thereof, an enlarged diameter recess extending from one face into said planar body and being concentric with said central bore but spaced from the opposite face thereof to define a shoulder, said tabs complementing recesses formed in said planar body adjacent to said enlarged diameter recess, whereby the cannulated dilator fits into said tool and said cannulated dilator engages said shoulder to permit the user to insert said cannulated dilator into said access hole and rotate same as it progresses into said access hole and a cannula for insertion into said access hole to permit a surgical procedure after the cannulated dilator has been removed.

3. The combination of a cannulated dilator and a dilator retractor wherein said cannulated dilator includes indicia for measuring the depth of an access hole formed in a patient for medical procedure and said dilator retractor being made from a cuttable material and being dimensioned larger in length than is anticipated of any depth of said access hole of the body of any patient that is anticipated in the medical procedure, the dilator retractor being cuttable commensurate with the depth of said access hole as measured by said cannulated dilator for sizing said dilator retractor to a length that is shorter than the original length of the dilator retractor prior to being inserted into the access hole so as to be utilized for performing the medical procedure whereby said dilator retractor is sized for the anatomy of the patient.

4. The combination of a cannulated dilator and a dilator retractor as claimed in claim 3 wherein said dilator retractor is made from a plastic material.

5. The combination of a cannulated dilator and a dilator retractor as claimed in claim 4 wherein said dilator retractor is made from a transparent material.

6. The combination of a cannulated dilator and dilator retractor as claimed in claim 3 including an annular clamp, said clamp being dimensioned to fit said dilator retractor and means including a bracket extending from said annular clamp adapted to support the dilator retractor to a rigid member.

7. The combination of a cannulated dilator and dilator retractor as claimed in claim 6 wherein said clamp is split through a portion thereof to define a gap between the ends adjacent the split, an adjustment for enlarging or decreasing said gap and the inner diameter portion surrounding the dilator retractor for securing said annular clamp to the dilator retractor and including means adapted to support the dilator retractor to a rigid member.

8. The combination of a cannulated dilator and dilator retractor as claimed in claim 6 including an elongated fixture having a circular cross section and made from a cuttable plastic material, and means to cut said dilator retractor an amount commensurate with the measurement attained by said cannulated retractor and the width of said annular clamp.

9. The combination of a cannulated dilator and dilator retractor as claimed in claim 8 wherein said elongated fixture includes a series of axially spaced grooves spaced a predetermined amount, said dilator retractor being transparent and fitting over said elongated fixture for the spaced grooves to be visible wherein the selection of said annular grooves determines the length of the dilator retractor to be cut.

10. The combination of a cannulated dilator and dilator retractor as claimed in claim 3 including a pusher tool having an elongated circular body, a central bore having a dimension to complement the outer diameter of said cannulated dilator, and a bottom surface overlying the end of said dilator retractor so that when said pusher tool is pushed into the body cavity the dilator retractor is forced into the body cavity and the central bore slides over said cannulated dilator.

11. The combination of a cannulated dilator and dilator retractor as claimed in claim 10 wherein said pusher tool is integral with said elongated fixture.

12. The combination of a cannulated dilator and dilator retractor, said cannulated dilator being in the series of the last cannulated dilator for enlarging the access hole in the body of a patient, at least one of said cannulated dilators having an elongated body, indicia on said elongated body indicative of a measurement of depth for measuring the depth of the access hole, said dilator retractor including a series of dilator retractors each having different lengths, whereby the dilator retractor for use in the access hole is selected from said series of dilator retractors that is commensurate with the measurement of said cannula(d dilator as obtained from said indicia when inserted into said access hole for defining a working space for performing a medical procedure when the cannulated dilator has been removed.

13. The method of sizing the length of a cannula to fit the depth of an access hole formed in the body of a patient including the steps of:
 i. providing a cannula that is oversized in length;
 ii. providing a cannulated dilator that is in the last of a series of cannulated dilators used for enlarging the access hole with indicia of a scale for measuring a length;
 iii. measuring the depth of the access hole by inserting the cannulated dilator obtained in the step of providing a cannulated dilator into the access hole to ascertain the depth;
 iv. cutting the cannula to the size obtained in the step of measuring before being inserted into the access hole; and
 v. inserting the cannula obtained in the step of cutting into the access hole over the cannulated dilator and removing the cannulated dilator to define a working space to perform a medical procedure.

14. The method as claimed in claim 13 including the step of providing a template made from a cuttable material that is dimensioned to fit into the cannula;
 i. inserting the template into the cannula;
 ii. cutting the cannula and template at the length commensurate with the access hole.

15. The method as claimed in claim 14 including the provision of including markings on said template graduated to a scale commensurate with the scale of the indicia on the cannulated dilator; and the cannula being transparent so that the scale on the fixture is visible.

16. The method as claimed in claim 14 including a clamp to fit the end of the cannula; cutting in the step of cutting the cannula to a length that includes the width of the clamp.

17. The method as claimed in claim 14 including the step of providing a tool for engaging the proximal end of the cannulated dilator and inserting the cannulated dilator by pushing and turning the tool.

18. The method as claimed in claim 14 including the step of providing a tool for engaging said cannula for pushing said cannula into the access hole.

19. The method of sizing the length of a cannula to fit the depth of an access hole formed in the body of a patient including the steps of:
   i. providing a series of different length cannulas;
   ii. providing a cannulated dilator with indicia of a scale for measuring a length;
   iii. measuring the depth of the access hole by inserting the cannulated dilator into the access hole to ascertain the depth;
   iv. selecting from said different length cannulas obtained in the step of providing a series of different length cannulas the length correlating to the length obtained in the step of measuring before inserting said selected cannula; and
   v. inserting said the cannula obtained in the step of selecting from said different length cannulas into said access hole for defining a working chamber for performing the medical procedure.

20. The combination of a cannulated dilator and dilator retractor as claimed in claim 12 including an annular clamp, said clamp being dimensioned to fit any of said dilator retractor from said series of said dilator retractors and a bracket extending from said annular clamp adapted to support the dilator retractor to a rigid member.

21. The combination of a cannulated dilator and dilator retractor as claimed in claim 12 wherein each of said cannulated dilator has a proximal end and a tool engagement portion formed thereon, a tool having an engagement portion complementing the tool engagement portion of the cannulated dilator adapted to fit thereon for rotation and applying leverage on said cannulated dilator for insertion thereof into the body cavity.

22. The combination of a cannulated dilator and dilator retractor, said cannulated dilator having an elongated body, said cannulated dilator for obtaining the measurement of depth of an access hole formed in a body, said dilator retractor including a series of dilator retractors having different lengths, whereby the dilator retractor for use in the access hole is selected from said series of dilator retractors that is commensurate with the measurement obtained from said cannulated dilator when extended into said access hole.

23. The combination of a cannulated dilator and dilator retractor as claimed in claim 12 wherein said dilator retractor is made form a plastic material.

24. The combination of a cannulated dilator and dilator retractor as claimed in claim 23 wherein said dilator retractr is made form a transparent material.

* * * * *